(12) United States Patent
Paul et al.

(10) Patent No.: US 12,409,087 B2
(45) Date of Patent: Sep. 9, 2025

(54) USER CONTROLS FOR PATIENT SUPPORT APPARATUS HAVING LOW HEIGHT

(71) Applicant: Stryker Corporation, Kalamazoo, MI (US)

(72) Inventors: Anish Paul, Kalamazoo, MI (US); Jeffrey S. Dunfee, II, Kalamazoo, MI (US); Ryan Ross, New Carlisle, IN (US)

(73) Assignee: Stryker Corporation, Portage, MI (US)

( * ) Notice: Subject to any disclaimer, the term of this patent is extended or adjusted under 35 U.S.C. 154(b) by 1301 days.

(21) Appl. No.: 17/125,058

(22) Filed: Dec. 17, 2020

(65) Prior Publication Data

US 2021/0100705 A1 Apr. 8, 2021

Related U.S. Application Data

(63) Continuation of application No. 16/210,872, filed on Dec. 5, 2018, now Pat. No. 10,898,399.

(Continued)

(51) Int. Cl.
*A61G 7/018* (2006.01)
*A61B 5/00* (2006.01)
(Continued)

(52) U.S. Cl.
CPC ............. *A61G 7/018* (2013.01); *A61G 7/012* (2013.01); *A61G 7/0528* (2016.11); *A61G 7/08* (2013.01);
(Continued)

(58) Field of Classification Search
CPC ...... A61G 7/012; A61G 7/018; A61G 7/0506; A61G 7/051; A61G 7/054; A61G 7/0514; A61G 7/0524; A61G 7/0528; A61G 7/08; A61G 7/1013; A61G 7/1046; A61G 7/1067; A61G 2203/32; A61G 2203/36; A61G 2203/40; A61G 2203/42; A61B 5/6892; A61B 2562/0252; A61B 2017/00207; G16H 40/60
(Continued)

(56) References Cited

U.S. PATENT DOCUMENTS

| 4,680,790 A | * | 7/1987 | Packard | ............... | A61G 7/0524 340/286.07 |
| 5,592,153 A | * | 1/1997 | Welling | .................. | G10L 15/26 340/286.07 |

(Continued)

FOREIGN PATENT DOCUMENTS

KR 20230125453 A * 8/2023 ........... A61G 7/0507

*Primary Examiner* — David R Hare
(74) *Attorney, Agent, or Firm* — Howard & Howard Attorneys PLLC

(57) ABSTRACT

A patient support apparatus comprises a support structure. The support structure comprises a base and a patient support deck coupled to the base. The patient support deck comprises a patient support surface capable of articulating to adjust positioning of a patient supported thereon, a lift system configured to adjust a height of the patient support deck relative to the base, and a user interface system coupled to the support structure and comprising an elongated member and a user interface coupled to the elongated member. The user interface is configured to receive inputs from a user to control a function of the patient support apparatus.

18 Claims, 6 Drawing Sheets

Related U.S. Application Data

(60) Provisional application No. 62/607,956, filed on Dec. 20, 2017.

(51) Int. Cl.
  *A61G 7/012* (2006.01)
  *A61G 7/05* (2006.01)
  *A61G 7/08* (2006.01)
  *A61G 7/10* (2006.01)

(52) U.S. Cl.
  CPC .......... *A61G 7/1013* (2013.01); *A61B 5/6892* (2013.01); *A61B 2562/0252* (2013.01); *A61G 7/0506* (2013.01); *A61G 7/051* (2016.11); *A61G 7/0514* (2016.11); *A61G 7/0524* (2016.11); *A61G 7/1046* (2013.01); *A61G 7/1067* (2013.01); *A61G 2203/32* (2013.01); *A61G 2203/36* (2013.01); *A61G 2203/40* (2013.01); *A61G 2203/42* (2013.01)

(58) Field of Classification Search
  USPC .......................................................... 5/613
  See application file for complete search history.

(56) References Cited

U.S. PATENT DOCUMENTS

| | | | |
|---|---|---|---|
| 6,677,969 B1 * | 1/2004 | Hongo | G06F 3/017 |
| | | | 715/863 |
| 6,772,850 B1 | 8/2004 | Waters et al. | |
| 7,419,019 B1 | 9/2008 | White et al. | |
| 7,886,377 B2 | 2/2011 | Hamberg et al. | |
| 9,205,009 B2 * | 12/2015 | Koors | A61G 7/012 |
| 9,259,369 B2 | 2/2016 | Derenne et al. | |
| 9,827,062 B2 | 11/2017 | Bally et al. | |
| 10,290,373 B2 * | 5/2019 | Jäger | G05B 15/02 |
| 10,720,237 B2 * | 7/2020 | Dobai | G16H 40/40 |
| 2007/0241529 A1 * | 10/2007 | Stroh | A61G 7/08 |
| | | | 280/202 |
| 2011/0304541 A1 * | 12/2011 | Dalal | G06F 3/0346 |
| | | | 345/158 |
| 2013/0200579 A1 | 8/2013 | Abernethy et al. | |
| 2013/0219382 A1 | 8/2013 | Parsons et al. | |
| 2014/0049465 A1 * | 2/2014 | Tremaine | G16H 40/63 |
| | | | 345/156 |
| 2014/0094997 A1 * | 4/2014 | Hyde | G05D 1/0246 |
| | | | 348/148 |
| 2017/0143565 A1 * | 5/2017 | Childs | A61G 7/015 |
| 2018/0153752 A1 * | 6/2018 | Kostic | G06F 3/04817 |
| 2018/0369039 A1 * | 12/2018 | Bhimavarapu | A61G 7/018 |
| 2019/0183703 A1 | 6/2019 | Paul et al. | |

* cited by examiner

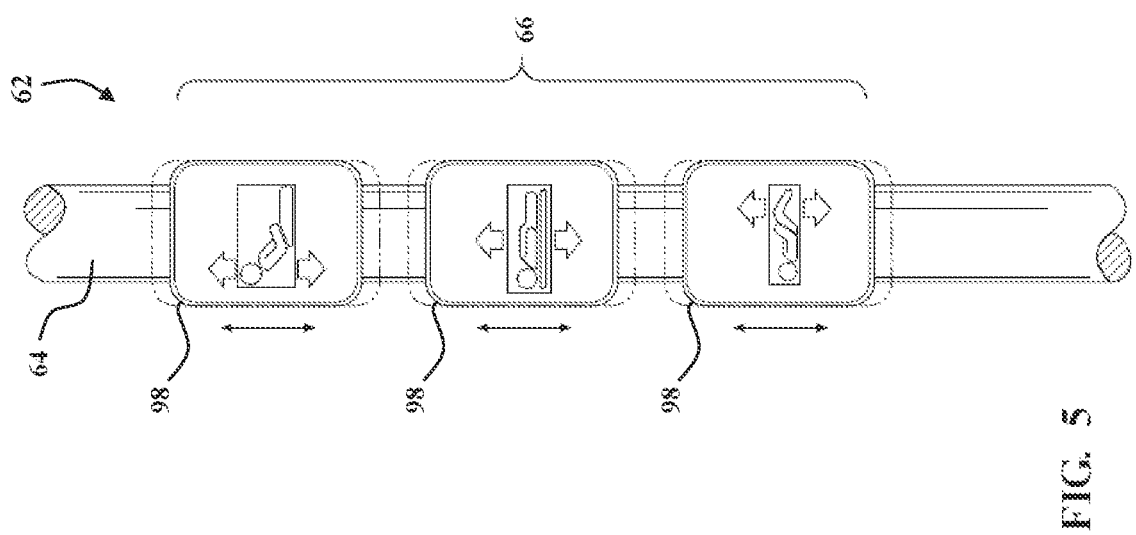

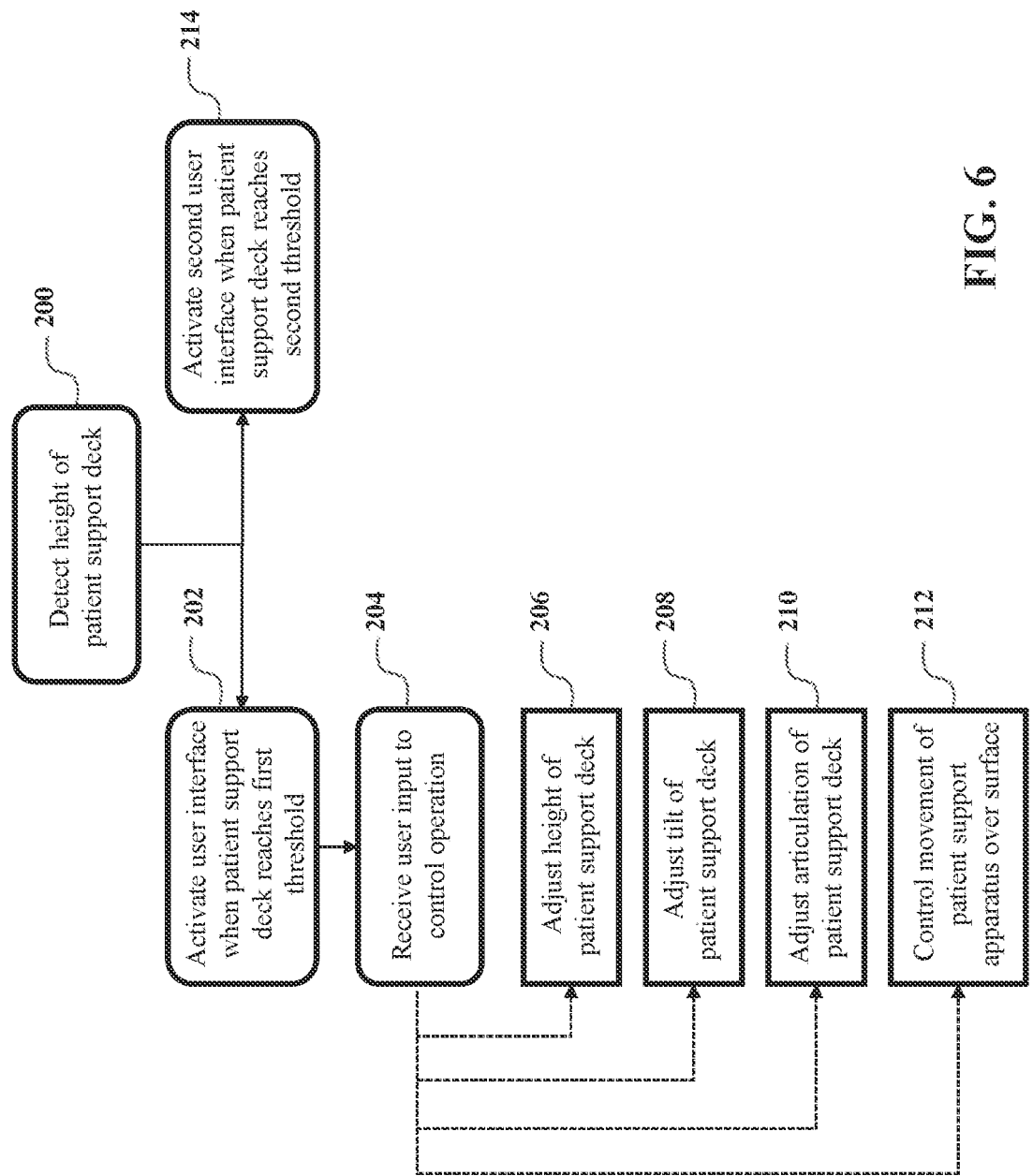

USER CONTROLS FOR PATIENT SUPPORT APPARATUS HAVING LOW HEIGHT

CROSS-REFERENCE TO RELATED APPLICATIONS

The subject patent application is a Continuation of U.S. patent application Ser. No. 16/210,872, filed on Dec. 5, 2018 which claims priority to and all the benefits of U.S. Provisional Patent Application No. 62/607,956 filed on Dec. 20, 2017, the disclosures of each of which are hereby incorporated by reference in their entirety.

BACKGROUND

Patient transport systems facilitate care of patients in a health care setting. Patient transport systems comprise patient support apparatuses (e.g., beds, stretchers, cots, tables, wheelchairs, chairs, recliners, etc.). Patient support apparatuses comprise a base, a support frame upon which the patient is supported, a lift system for lifting and lowering the support frame relative to the base, and a control interface for controlling the lift system. Because the lift system lifts and lowers the support frame, the control interface of the lift system must be accessible to a caregiver at different heights. However, the control interface may be difficult to access when it is located on the support frame itself, due to the varying heights of the support frame. For example, when the support frame is at a low height, for purposes such as fall prevention, the control interface may be too low for the caregiver to reach easily or ergonomically.

A patient support apparatus having user controls designed to overcome at least one or more of the aforementioned disadvantages is desired.

BRIEF DESCRIPTION OF THE DRAWINGS

FIG. 5 is a front view of a user interface system for the patient support apparatus.

FIG. 6 is a flowchart of a method of operating the control system according to one example.

DETAILED DESCRIPTION

I. Patient Support Apparatus Overview

Figure 1:
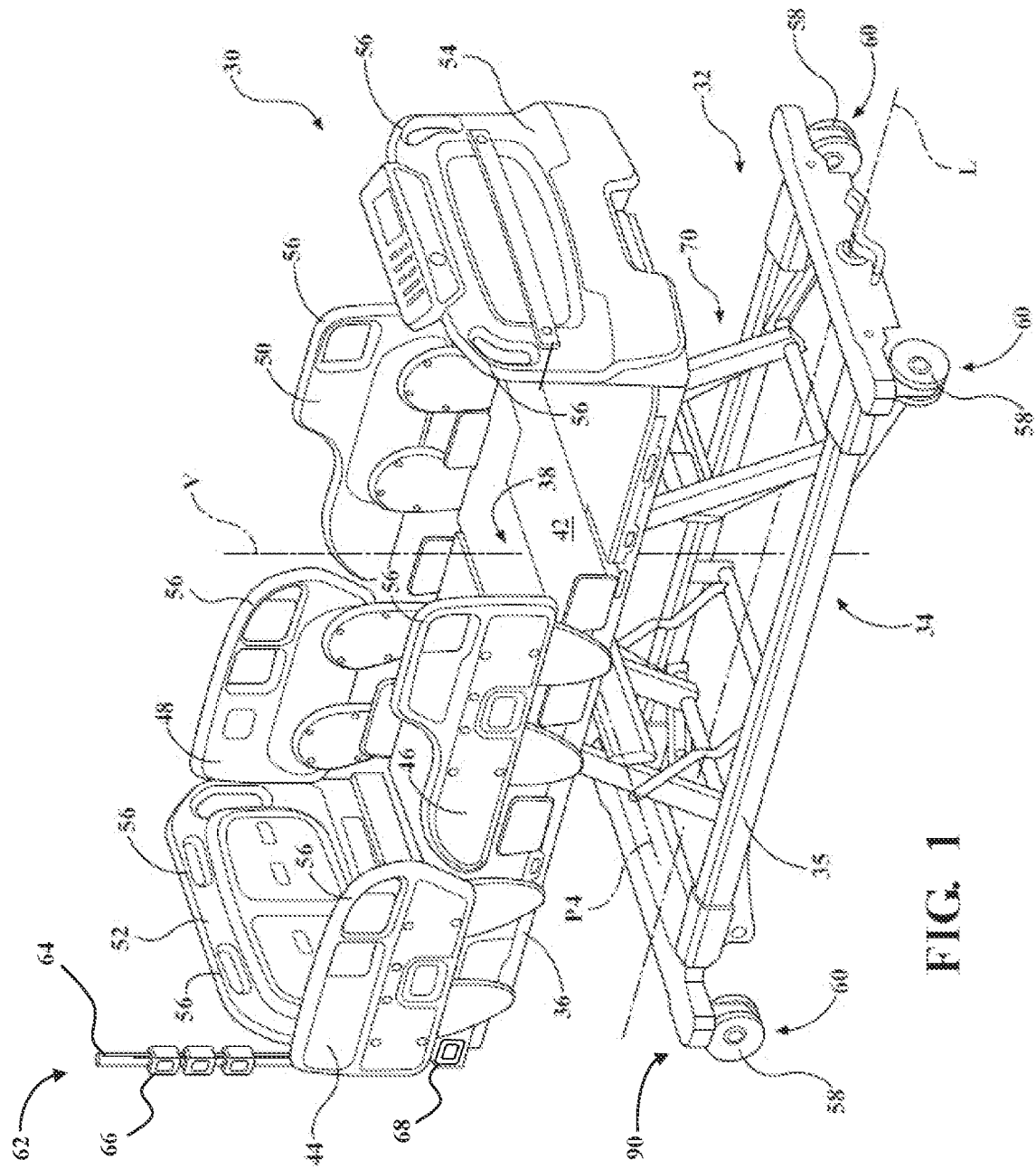
FIG. 1 is perspective view of a patient support apparatus according to one example.

Referring to FIG. 1, a patient support apparatus 30 is shown for supporting a patient in a health care setting. The patient support apparatus 30 illustrated in FIG. 1 comprises a hospital bed. In other embodiments, however, the patient support apparatus 30 may comprise a stretcher, cot, table, wheelchair, chair, or similar apparatus utilized in the care of a patient.

A support structure 32 defines various components of the chassis and/or body of the patient support apparatus 30. Often, the support structure 32 provides support for the patient. The support structure 32 illustrated in FIG. 1 comprises a base 34 and a support frame 36. The base 34 comprises a base frame 35. The support frame 36 is spaced above the base frame 35 in FIG. 1. The support structure 32 also comprises a patient support deck 38 disposed on the support frame 36. The patient support deck 38 comprises several sections, some of which are pivotable relative to the support frame 36, such as a fowler section, a seat section, a thigh section, and a foot section. The patient support deck 38 provides a patient support surface 42 upon which the patient is supported.

A mattress (not shown) is disposed on the patient support deck 38 during use. The mattress comprises a secondary patient support surface upon which the patient is supported. The base 34, support frame 36, patient support deck 38, and patient support surfaces 42 each have a head end and a foot end corresponding to designated placement of the patient's head and feet on the patient support apparatus 30. The base 34 comprises a longitudinal axis L along its length from the head end to the foot end. The base 34 also comprises a vertical axis V arranged crosswise (e.g., perpendicularly) to the longitudinal axis L along which the support frame 36 is lifted and lowered relative to the base 34. The construction of the support structure 32 may take on any design not limited to that specifically set forth above. In addition, the mattress may be omitted in certain embodiments, such that the patient rests directly on the patient support surface 42.

The support structure 32 comprises side rails 44, 46, 48, 50 coupled to the support frame 36 and thereby supported by the base 34. A first side rail 44 is positioned at a right head end of the support frame 36. A second side rail 46 is positioned at a right foot end of the support frame 36. A third side rail 48 is positioned at a left head end of the support frame 36. A fourth side rail 50 is positioned at a left foot end of the support frame 36. If the patient support apparatus 30 is a stretcher or a cot, there may be fewer side rails. The side rails 44, 46, 48, 50 are movable between a raised position in which they block ingress and egress into and out of the patient support apparatus 30, one or more intermediate positions, and a lowered position in which they are not an obstacle to such ingress and egress. In still other configurations, the patient support apparatus 30 may not include any side rails.

The support structure 32 comprises a headboard 52 and a footboard 54, which are coupled to the support frame 36. In other embodiments, when the headboard 52 and footboard 54 are included, the headboard 52 and footboard 54 may be coupled to other locations on the patient support apparatus 30, such as the base 34. In still other embodiments, the patient support apparatus 30 does not include the headboard 52 and/or the footboard 54.

Caregiver interfaces 56, such as handles, are shown integrated into the footboard 54 and side rails 44, 46, 48, 50 to facilitate movement of the patient support apparatus 30 over floor surfaces. Additional caregiver interfaces 56 may be integrated into the headboard 52 and/or other components of the patient support apparatus 30. The caregiver interfaces 56 are graspable by the caregiver to manipulate the patient support apparatus 30 for movement.

Other forms of the caregiver interface 56 are also contemplated. The caregiver interface may comprise one or more handles coupled to the support frame 36. The caregiver interface may simply be a surface on the patient support apparatus 30 upon which the caregiver logically applies force to cause movement of the patient support apparatus 30 in one or more directions, also referred to as a push location. This may comprise one or more surfaces on the support frame 36 or base 34. This could also comprise one or more surfaces on or adjacent to the headboard 52, footboard 54, and/or side rails 44, 46, 48, 50. In other embodiments, the caregiver interface may comprise separate handles for each hand of the caregiver. For example, the caregiver interface may comprise two handles.

A drive system 90 influences motion of the patient support apparatus 30 during transportation over a floor surface. The drive system 90 may have one or more motors (not shown), or may be non-powered. The drive system 90 is integrated into the patient support apparatus 30. The drive system 90 may comprise wheels 58, which are coupled to the base 34 to facilitate transport over the floor surfaces. The wheels 58 are arranged in each of four quadrants of the base 34 adjacent to corners of the base 34. In the embodiment shown, the wheels 58 are caster wheels able to rotate and swivel relative to the support structure 32 during transport. Each of the wheels 58 forms part of a caster assembly 60. Each caster assembly 60 is mounted to the base 34. It should be understood that various configurations of the caster assemblies 60 are contemplated. In addition, in some embodiments, the wheels 58 are not caster wheels and may be non-steerable, steerable, non-powered, powered, or combinations thereof. Additional wheels are also contemplated. For example, the patient support apparatus 30 may comprise four non-steerable, non-powered wheels, along with one or more powered wheels. In some cases, the patient support apparatus 30 may not include any wheels.

In other embodiments, one or more auxiliary wheels (powered or non-powered), which are movable between stowed positions and deployed positions, may be coupled to the support structure 32. In some cases, when these auxiliary wheels are located between caster assemblies 60 and contact the floor surface in the deployed position, they cause two of the caster assemblies 60 to be lifted off the floor surface thereby shortening a wheel base of the patient support apparatus 30. A fifth wheel may also be arranged substantially in a center of the base 34.

Further details of a powered drive system that may be used with the patient support apparatus 30 disclosed herein are disclosed in U.S. Pat. No. 6,772,850, issued to Waters et al. and entitled POWER ASSISTED WHEELED CARRIAGES, as well as U.S. Pat. No. 9,259,369, issued to Derenne et al. and entitled POWERED PATIENT SUPPORT APPARATUS, the complete disclosures of which are both hereby incorporated herein by reference.

II. User Control Techniques for Low Height

As shown in FIG. 1, a user interface system 62 is coupled to the support structure 32. The user interface system 62 may comprise an elongated member 64. The elongated member 64 may comprise a vertically extending member, i.e., extending upwards along axis V. The elongated member 64, in one embodiment, is a pole, and more specifically, may be an IV pole.

The user interface system 62 further comprises a user interface 66 coupled to the elongated member 64. The user interface 66 may be configured to receive inputs from a user to control one or more functions of the patient support apparatus 30.

Figure 2:
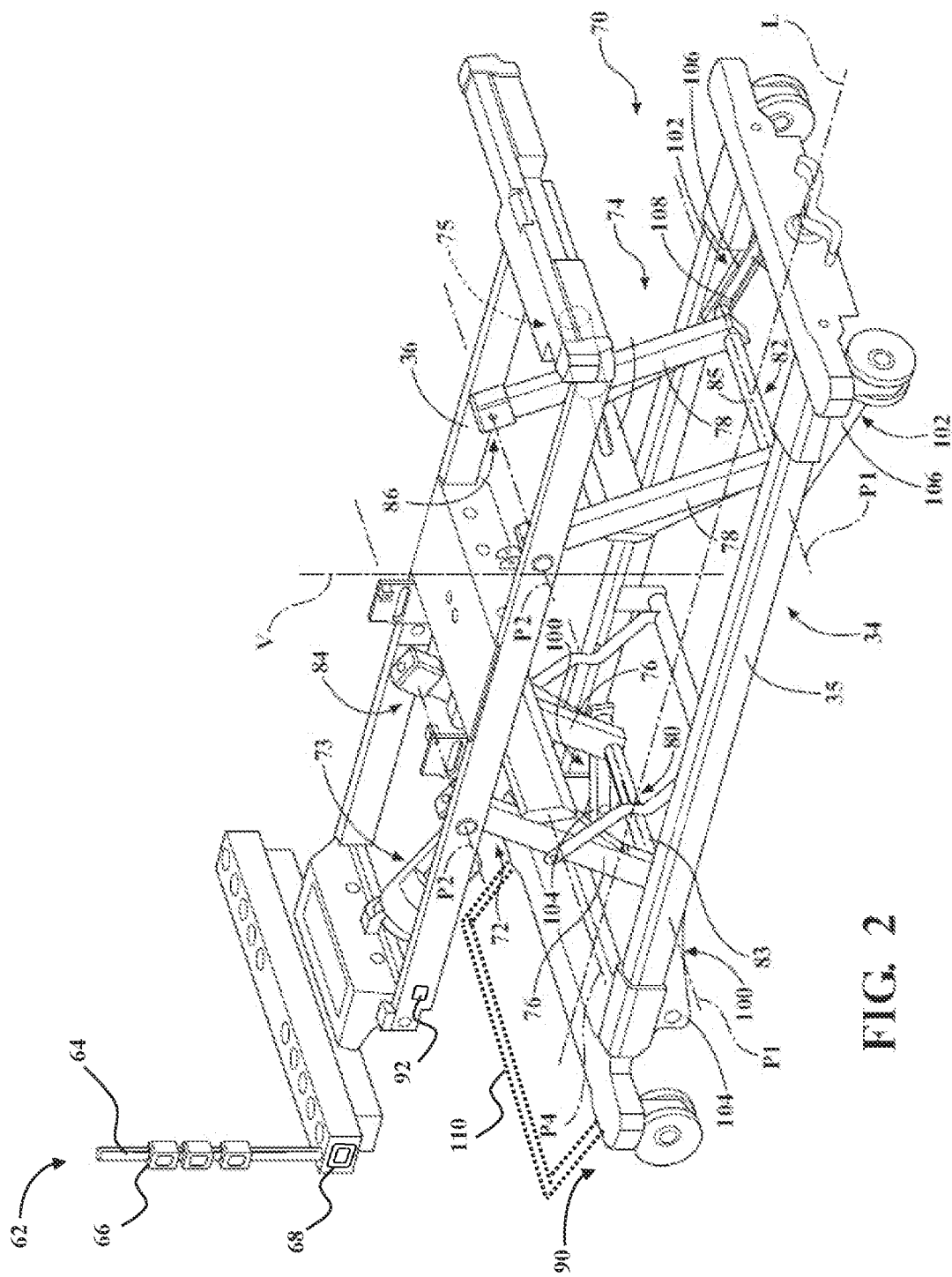
FIG. 2 is a perspective view of a lift system of the patient support apparatus at a maximum height.

The elongated member 64 as shown in FIG. 2 has a cylindrical cross-section. However, the elongated member may have any other cross-section, such as rectangular, square, etc. The elongated member 64 has a height defined between a proximal end, which is coupled to the support structure 32 and a distal end, which is freely positioned in space. As will be understood form the Figures and the examples described herein, the height of the elongated member 64 is specifically defined to enable the user interface 66 to remain at an ergonomically suitable position whether the support frame 36 of the patient support apparatus 30 is lifted to a maximum height or lowered to a minimum height.

As shown in FIG. 2, the patient support apparatus 30 may further comprise a second user interface 68 coupled to the support structure 32. In various embodiments, the second user interface 68 may be physically coupled to, for example, the footboard 52, the side rails 44, 46, 48, 50, or any other suitable placement on the support structure 32. The second user interface 68 may be configured to receive inputs from a user to control one or more functions of the patient support apparatus 30.

Figure 3:
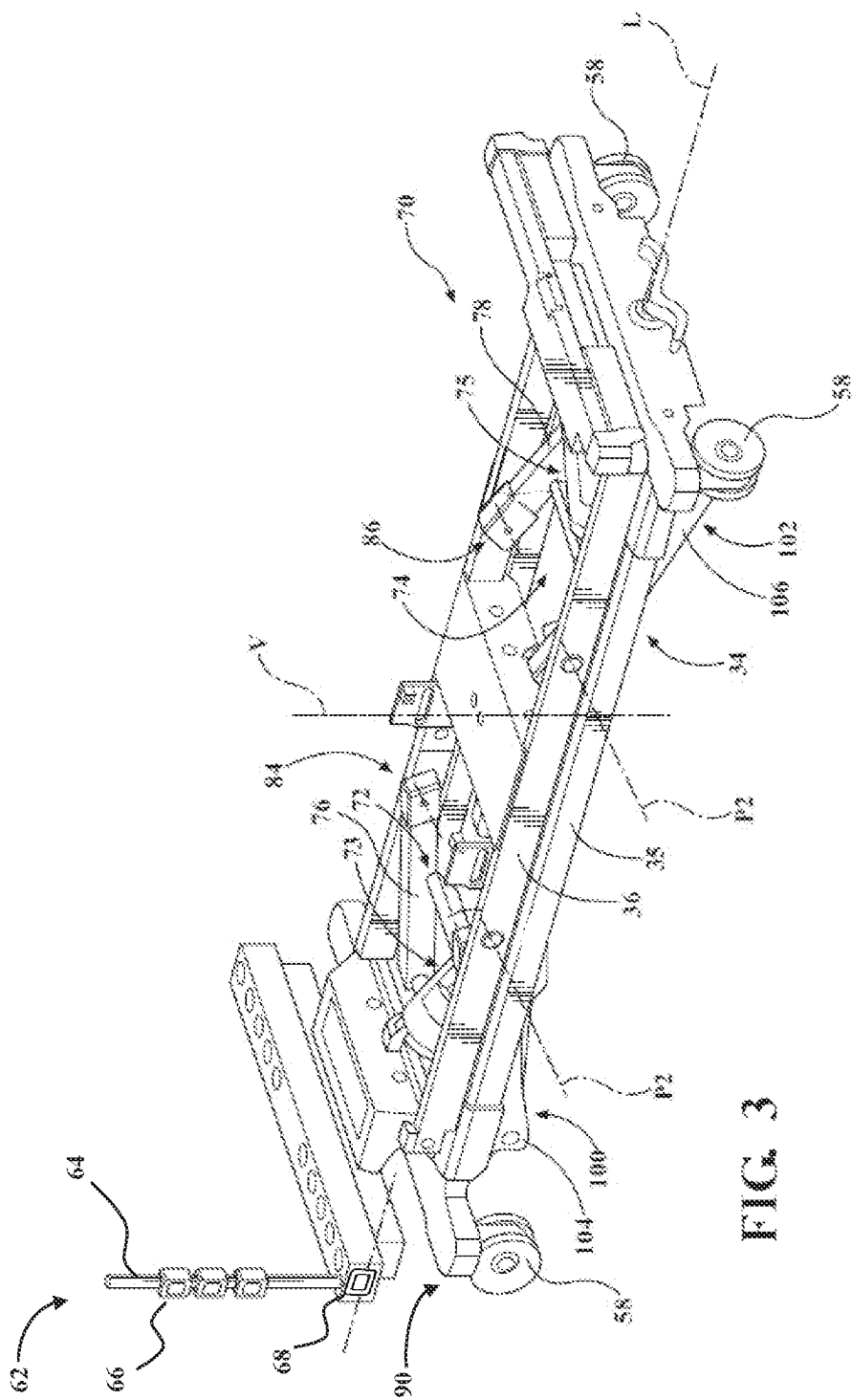
FIG. 3 is a perspective view of the lift system of the patient support apparatus at a minimum height.

Referring to FIGS. 2 and 3, the patient support apparatus 30 comprises a lift system 70 that operates to lift and lower the support frame 36 relative to the base 34. The lift system 70 is configured to move the support frame 36 from the minimum height (shown in FIG. 3) to the maximum height (shown in FIG. 2), or to any desired position in between.

In one example, as shown, the lift system 70 comprises head end and foot end lift members 72, 74. First and second actuators 73, 75 move the lift members 72, 74 to lift and lower the support frame 36 relative to the base 34. The first actuator 73 is coupled to the head end lift member 72. The second actuator 75 is coupled to the foot end lift member 74. The actuators 73, 75 operate to pivot their respective lift member 72, 74 about fixed upper pivot axes P2 to lift and lower the support frame 36 relative to the base 34, as described further below.

The actuators 73, 75 comprise linear actuators, rotary actuators, or other types of actuators. The actuators 73, 75 may be electrically operated and/or may be hydraulic. In the embodiment shown, the actuators 73, 75 are electro-hydraulic, linear actuators, such as compact electro-hydraulic actuators. In other embodiments, the actuators 73, 75 can be electric, linear actuators. It is contemplated that, in some embodiments, only one lift member and one associated actuator may be employed, e.g., to raise only one end of the support frame 36.

The lift members 72, 74 comprise a pair of head end lift legs 76 and a pair of foot end lift legs 78 pivoted by the actuators 73, 75 about the fixed upper pivot axes P2. In other embodiments, each of the lift members 72, 74 may comprise a single lift leg. In still other embodiments, other types of lifting members capable of lifting and lowering the support frame 36 may be employed. The lift members 72, 74 may be identical in form or may have different forms. For instance, one of the lift members 72, 74 may be a single lift leg, while the other of the lift members 72, 74 may comprise part of a scissor-type mechanism. It should be appreciated that each of the lift members 72, 74 may be formed in a unitary construction or may be separate pieces fastened together.

The lift members 72, 74 comprise first end sections 80, 82 movably coupled to the base 34. In particular, the first end sections 80, 82 are connected to guided bodies 108 that slide in head end and foot end guides 100, 102 relative to the base 34 during the lifting and lowering of the support frame 36, i.e., when the actuators 73, 75 pivot the lift members 72, 74 about the fixed upper pivot axes P2. In the embodiment shown, the first end sections 80, 82 comprise first ends of the lift legs 76, 78 and a support member 83, 85 interconnecting each pair of the lift legs 76, 78, respectively, at their first ends. In the embodiment shown, the support members 83, 85 are rigidly fixed to the lift legs 76, 78 to move with the lift legs 76, 78. The support members 83, 85 define a moving lower pivot axis P1 about which the support members 83, 85 pivot as the first end sections 80, 82 slide relative to the base 34. In other embodiments, the lift legs 76, 78 may pivot relative to the support members 83, 85.

The lift members 72, 74 extend from the first end sections 80, 82 to second end sections 84, 86. The second end sections 84, 86 are pivotally connected to the support frame 36 at the fixed upper pivot axes P2 for pivoting relative to the support frame 36. In the embodiment shown, the second end sections 84, 86 comprise second ends of the lift legs 76, 78. The fixed upper pivot axes P2 lie in a common plane perpendicular to the vertical direction when the support frame 36 is at the minimum height or the maximum height.

The guides 100, 102 are arranged to guide the movement of the first end sections 80, 82 when the actuators 73, 75 pivot the lift members 72, 74 about the fixed upper pivot axes P2 to lift and lower the support frame 36 relative to the base 34. The head end guides 100 guide movement of the head end lift member 72. The foot end guides 102 guide movement of the foot end lift member 74. In the embodiment shown, four guides 100, 102 are provided. The four guides 100, 102 comprise a pair of head end guide tracks 104 and a pair of foot end guide tracks 106. The guide tracks 104, 106 are fixed to the base 34 and have a hollow, elongated shape. In particular, the guide tracks 104, 106 are shown being formed of rectangular tubing. In other embodiments, the guides 100, 102 may assume other forms or shapes capable of guiding movement of the first end sections 80, 82 of the lift members 72, 74.

While the lift system 70, as shown in FIGS. 2 and 3, has been described in detail, those skilled in the art appreciate that the lift system 70 may be implemented according to various other different configurations beside that shown in FIGS. 2 and 3.

A height sensor 92 may be coupled to the support frame 36 (as shown in FIG. 2), the patient support deck 38, or any other suitable location. The height sensor 92 may detect a height of the patient support deck 38 relative to the base 34. The height sensor 92 may comprise a 3-D accelerometer, a 3-D gyroscope, an inclinometer, or other suitable type of sensor configured to directly or indirectly measure height changes.

Figure 4:
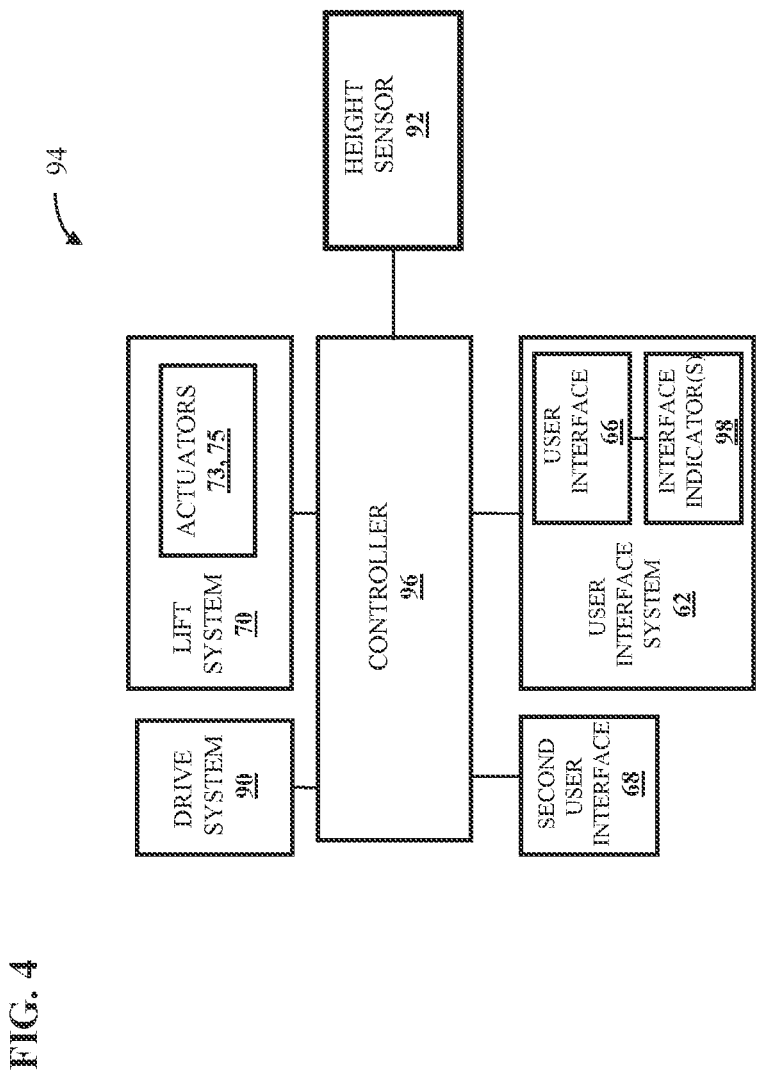
FIG. 4 is a block diagram of one example of a control system for the patient support apparatus.

Referring now to FIG. 4, a block diagram of a control system 94 usable with the patient support apparatus 30 is shown, according to one embodiment. As described, when the patient support deck 38 is at a low height, it is desirable for the user controls to be located at a higher level that is more easily accessible to the user. Therefore, when the lift system 70 lowers the patient support deck 38 relative to the base 34, the height sensor 92 may detect that the height of the patient support deck 38 is below a predefined threshold or at the minimum height. In other examples, the height sensor 92 may identify that the support deck 38 is in the process of being lowered.

The height sensor 92 may indicate such readings to a controller 96 of the patient support apparatus 30. The controller 96 may be in communication with and may control any suitable components of the patient support apparatus 30, such as the electrical or electromechanical components described herein. The controller 96 may comprise any suitable signal processing means, computer executable instructions or software modules stored in a non-transitory memory wherein the executable instructions or modules may be executed by a processor, or the like. Additionally, or alternatively, the controller 96 may comprise a microcontroller, a processor, one or more integrated circuits, logic parts, and the like for enabling the same. The controller 96 may have any suitable configuration for enabling performance of various tasks related to operation of the patient support apparatus 30, such as those described below. The controller 96 may be located at any suitable location of the patient support apparatus 30.

In other examples, the controller 96 may determine that the support deck 38 is at a low/minimum height based on input from sensors besides the height sensor 92. For instance, the controller 96 may receive readings from the any of the moveable components of the lift system 70, as described above. Additionally, the controller 96 may infer the height of the support deck 38 after executing height adjustment commands triggered from any of the user interfaces 66, 68.

The user interface 66 coupled to the elongated member 64 may be activated by the controller 96 upon the controller 96 determining that the support deck 38 is at a low/minimum height. Therefore, even when the patient support deck 38 is at a low height, controls may be ergonomically accessible to the user.

When the user interface 66 is activated, the user interface 66 is configured to receive input from the user. The user interface 66 may generate an input signal based on the received input and send the input signal to the controller 96. The user interface 66 may receive inputs from the user to control operation of the lift system 70 or to control operation of one or more other powered devices on the patient support apparatus 30 to one or more of: (1) adjust the height of the patient support deck 38 relative to the base 34; adjust a tilt of the patient support deck 38 relative to the base 34; (3) control articulation of the patient support surface 38; (4) control movement of the patient support apparatus 30 over a floor surface; (5) control operation of a patient scale; and (6) control electronic brakes or other mobility system. The user interface 66 may be used to control operation of any powered device associated with the patient support apparatus 30.

In one embodiment, in addition to or instead of receiving inputs from the user to control operation of the lift system 70, the user interface 66 may receive inputs from the user to activate a bed exit detection system to generate an alarm in certain situations. For example, the alarm may indicate that a patient has exited the patient support apparatus 30.

When the lift system 70 raises the patient support deck 38, it may be desirable for the user controls to be located at a lower level that is more easily accessible to the user. Therefore, when the lift system 70 raises the patient support deck 38 relative to the base 34, the height sensor 92 may detect that the height of the patient support deck 38 is above the predefined threshold or at the maximum height. The height sensor 92 may indicate to the controller 96 that the patient support deck 38 is above the predefined threshold or at the maximum height. In other examples, the height sensor 92 may identify that the support deck 38 is in the process of being raised. In other examples, the controller 96 may determine that the support deck 38 is at a high/maximum height based on input from sensors besides the height sensor 92. For instance, the controller 96 may receive readings from the any of the moveable components of the lift system 70, as described above. Additionally, the controller 96 may infer the height of the support deck 38 after executing height adjustment commands triggered from any of the user interfaces 66, 68.

In such instances, the second user interface 68, which is disposed at a lower height relative to the user interface 66 coupled to the elongated member 64, may be activated by the controller 96 upon the controller 96 determining that the support deck 38 is at a high/maximum height. Therefore, even when the patient support deck 38 is at an elevated height, controls may be ergonomically accessible to the user.

When the second user interface 68 is activated, the second user interface 68 is configured to receive input from the user. The second user interface 68 may generate an input signal based on the received input and send the input signal to the controller 96. The second user interface 68 may receive inputs from the user to control operation of any of the aforementioned capabilities described with respect to the user interface 66.

In one embodiment, both the user interface 66 and the second user interface 68 are simultaneously activated, such that the user may choose to use the interface most conveniently accessible to the user based on the user's position and the position of the patient support deck 38. In an alternate embodiment, only one of the user interface 66 and the second user interface 68 is activated at a time, based on the position of the patient support deck 38. In yet another embodiment, the second user interface 68 is always activated, and the user interface 66 is activated only when the height of the patient support deck 38 is below the predefined threshold.

Referring now to FIG. 5, a front view of one example of the user interface system 62 is shown. The user interface 66 may comprise a movable interface configured to be translated along, tilted relative to, and/or rotated about the elongated member 64. For instance, in the illustrated embodiment, the user interface 66 may be a slidable input device configured to be translated along the elongated member 64 by the user. The arrows indicate upward and downward movement of the user interface 66 along the elongated member 64. In one version a spring may couple the user interface 66 to the elongated member 64 so that movement of the user interface 66 in either direction is returned to a neutral, home position. In this case, movement of the user interface 66 may engage one or more switches or other sensors when moved a predetermined distance in either direction.

In embodiments where the user interface system 62 comprises more than one movable interface 66, each movable interface 66 may be separately movable relative to the elongated member 64. In an alternate embodiment, the user interface 66 may be tiltable relative to a vertical axis of the elongated member 64. In another alternate embodiment, the user interface 66 may be a rotatable input device configured to be rotated about the elongated member 64 by the user. Combinations of various types of user interfaces 66 are also contemplated.

In one embodiment, the user interface 66 comprises a capacitive sensor. For example, capacitive sensors can be integrated into the elongated member 64 so that they are substantially flush with an outer surface of the elongated member to provide an essentially smooth outer surface. Such configuration provides a sanitary and easily cleanable surface suitable for hospital environments whereby the flush surface is free of any grooves thereby preventing accumulation of biomass or bacteria.

Capacitive sensors may also be raised slightly to provide some tactile identification to the user. Separate capacitive sensors can be employed to sense swiping with a user's finger or other body part to move parts of the patient support apparatus 30 in each direction—for example one capacitive sensor senses the user's finger to lift the support frame 36 and one capacitive sensor senses the user's finger to lower the support frame 36. In other embodiments, the user interface 66 comprises piezoelectric sensors coupled to the elongated member 64 to be actuated by the user, e.g., by contact with a user's finger. In this case, one piezoelectric sensor may sense the user's finger to lift the support frame 36 and one piezoelectric sensor may sense the user's finger to lower the support frame 36.

Referring again to FIG. 4, the user interface system 62 may be coupled to the controller 96. The controller 96 may determine a control attribute associated with the user interface 66. The control attribute may be one or more of: (1) force applied to the user interface 66 (e.g., sensed by spring tension or compression or sensed by pressure on the piezoelectric sensor or other load cell or pressure sensor), (2) displacement of the user interface 66 (e.g., sliding, tilting, or rotating as can be measured by a potentiometer), (3) velocity of the user interface 66 (e.g., of a slidable, tiltable, or rotatable interface, or velocity of a finger sliding on a capacitive sensor), and/or (4) acceleration of the user interface 66 (e.g., of a slidable, tiltable, or rotatable interface as measured by an accelerometer, or acceleration of a finger sliding on a capacitive sensor).

The controller 96 may operate the lift system 70, drive system 90, or other powered component of the patient support apparatus 30 based on the control attribute determined the controller 96 (by virtue of being coupled to one or more of the sensors, etc. described above). The operation of the lift system 70 may include one or more of: (1) displacement of the patient support deck 38 relative to the base 34, (2) velocity in moving the patient support deck 38, and (3) acceleration in moving the patient support deck 38. In other words, the operation of the lift system 70 may be proportional to or have some other predetermined relationship to the control attribute (e.g., force, displacement, velocity, acceleration). For example, the power applied to the actuators 73, 75 may be increased with an increase in the applied force.

The controller 96 receives input signals from the one or more user interfaces 66, 68 and can control operation of the actuator(s) 73, 75 so that the user is given the impression of moving a weightless part of the patient support apparatus 30. For example, the power applied to the actuators 73, 75 by the controller 96 can be tuned so that the amount of upward sliding (or velocity or acceleration) of the user interface 66 associated with lift/lower is proportional to the amount of lifting (or lowering in the other direction).

In one embodiment, as shown in FIGS. 4 and 5, the user interface 66 may further comprise one or more indicators 98 for indicating to the user that the user interface 66 is activated to perform the function of the patient support apparatus 30. The indicator 98 may be one or more of a visual indicator, a tactile indicator, and an audible indicator.

In one embodiment, the indicator 98 is a light ring surrounding the user interface 66, operated by an LED embedded within the user interface 66 (see FIG. 5). When a user interface 66 is activated by the controller 96 based on the detected height of the patient support deck 38, as described above, the LED turns the indicator 98 on, showing the activated state of the user interface 66 and indicating that the user may operate the user interface 66 to perform a function. When a user interface 66 is inactive, the LED turns the indicator 98 off, showing the inactive state of the user interface 66 and indicating that the user interface 66 is currently inoperable by the user due to the detected height of the patient support deck 38.

In other examples, the indicator 98 may indicate to the user information regarding an operation being executed from the user interface 66. For example, the indicator 98 may illuminate an upward arrow to indicate that a component is being raised using the user interface 66 and illuminate a downward arrow to indicate that a component is being lowered using the user interface 66.

The user interface 66 provides a quick and intuitive means of operating the lift system 70. As previously mentioned, placement of the user interface 66 at a higher level (e.g., on an IV pole mounted to the support frame 36), allows the user to easily access the controls. Moreover, use of a slidable or rotatable user interface 66 may provide coarse or fine motion control, depending on the desired level of control. The simple operation of the user interface 66 may be preferable over a complex user interface, for example, a menu-based interface with multiple screens or an interface with multiple buttons/options, which a user must navigate to find and indicate the desired function and which may be difficult to operate at low heights.

Various forms of the user interfaces 66, 68 are contemplated for being actuated by the user, such as the caregiver or the patient. Each user interface 66, 68 may be configured to be actuated in a variety of different ways, including but not limited to, mechanical actuation (hand, foot, finger, etc.), hands-free actuation (voice, foot, etc.), and the like. Each user interface 66, 68 may comprise a button, a gesture sensing device for monitoring motion of hands, feet, or other body parts of the caregiver (such as through a camera), a microphone for receiving voice activation commands, a foot pedal, and a sensor (e.g., infrared sensor such as a light bar or light beam to sense a user's body part, ultrasonic sensor, etc.). Additionally, the buttons/pedals can be physical buttons/pedals or virtually implemented buttons/pedals such as through optical projection (heads-up display) or on a touchscreen. It should be appreciated that any combination of user interfaces may also be utilized. The user interfaces 66, 68 may also be located on a portable electronic device (e.g., iWatch®, iPhone®, iPad®, or similar electronic devices or any other remote device/station in addition to a portable electronic device).

Referring to FIG. 6, a method of controlling movement of the patient support deck 38 relative to the base 34 is shown. In step 200, the method starts by first detecting a height of the patient support deck 38, i.e., by using the controller 96.

In a step 202, the user interface 66 is activated by the controller 96 to generate an input signal upon receiving input from a user to control an operation of the patient support apparatus 30 when a detected height of the patient support deck 38 is below a predefined threshold or at the minimum height.

In a step 204, the user interface 66 receives inputs from the user to control operation of the lift system 70 by the controller 96. In a step 206, the controller 96 directs the lift system 70 to adjust the height of the patient support deck 38 relative to the base 34. In a step 208, the controller 96 directs the lift system 70 to adjust a tilt of the patient support deck 38 relative to the base 34. In a step 210, the controller 96 directs the lift system 70 to control articulation of the patient support surface 38. In a step 212, the controller 96 directs the drive system 90 to control movement of the patient support apparatus 30 over a floor surface, such as by controlling power to a powered wheel of the patient support apparatus 30.

In a step 214, the second user interface 68 coupled to the support structure 32 is activated by the controller 96 to generate an input signal upon receiving input from the user to control an operation of the patient support apparatus 30 when the height sensor 92 detects the height of the patient support deck 38 to be above the predefined threshold or at the maximum height. Those skilled in the art appreciate that the method of controlling movement of the patient support deck 38 may include additional or alternative steps besides those shown in FIG. 6 in view of the spirit of the various examples described herein.

In yet another embodiment, the patient support apparatus 30 comprises a cot. The patient support apparatus 30 further comprises a bar 110 (see FIG. 2, shown in dotted lines) coupled to the base 34. In some embodiments, the bar 110 could be replaced by a pedal, button, or similar design, that is easily activated by foot (and provides an associated input signal to the controller 96). When the bar 110 is depressed, an input signal is received by the controller 96 to indicate that the patient support deck 38 should be raised. The controller 96 then generates a command signal to the lift system 70 so that the patient support deck 38 is lifted relative to the base 34 until it has reached a predefined initial height (e.g., 10 inches) as detected by the height sensor 92 (which is being monitored by the controller 96). This function allows the caregivers to raise the patient support apparatus 30 a small amount using their feet to avoid the strain from bending or kneeling to a very low level, as cots sometimes must be very low to the ground (e.g., when patients are being loaded/unloaded).

When the height sensor 92 coupled to the controller 96 detects that the patient support deck 38 is at or above the predefined initial height, the bar 110 may be deactivated (and thus rendered inoperable for any further raising of the patient support deck 38). Thereafter, raising of the patient support deck 38 is accomplished using the user interface 66, which may be located on the support frame 36, patient support deck 38, or elsewhere on the patient support apparatus 30. In other words, while the user steps on the bar 110, the controller 96 continuously monitors the current height via the height sensor 92 and, as long the current height is below the predefined initial height, the controller 96 continues raising the patient support deck 38 via the lift system 70, until a comparison of the current height and the predefined initial height by the controller 96 shows that the current height meets or exceeds the predefined initial height. Once the patient support deck 38 is at or above the predefined initial height, the user interface 66 may be used, as described above, to operate the lift system 70.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The invention is intended to be defined in the independent claims, with specific features laid out in the dependent claims, wherein the subject-matter of a claim dependent from one independent claim can also be implemented in connection with another independent claim.

What is claimed is:

1. A patient support apparatus comprising:
    a support structure comprising:
        a base, and
        a patient support deck coupled to the base, the patient support deck comprising a patient support surface capable of articulating to adjust positioning of a patient supported thereon;

a lift system configured to adjust a height of the patient support deck relative to the base; and a user interface system coupled to the support structure and comprising an elongated member a user interface movably coupled to the elongated member and configured to be one or more of translated along the elongated member and rotated about the elongated member, the user interface configured to receive inputs from a user and comprising a gesture sensing device for monitoring motion of the user, and including a controller to control a function of the patient support apparatus based on user engagement with the user interface system:

wherein the user interface system comprises a second user interface coupled to the support structure and configured to receive inputs from a user to control the function of the patient support apparatus; and wherein the user interface coupled to the elongated member is configured to be active to generate an input signal to control operation of the lift system upon receiving input from the user when a detected height of the patient support deck reaches a first threshold and to be inactive when the detected height of the patient support deck reaches a second threshold, wherein the second user interface is configured to be active to generate an input signal to control operation of the lift system upon receiving input from the user when the detected height of the patient support deck reaches the second threshold.

2. The patient support apparatus of claim 1, wherein the elongated member comprises an IV pole.

3. The patient support apparatus of claim 1, wherein the user interface is configured to receive inputs to control operation of the lift system to adjust one or more of:
height of the patient support deck relative to the base; and
tilt of the patient support deck relative to the base.

4. The patient support apparatus of claim 1, wherein the user interface is configured to receive inputs to control one or more of:
articulation of the patient support surface relative to the base;
movement of the patient support apparatus over a surface; and
activation of an alarm.

5. The patient support apparatus of claim 1, wherein the user interface comprises a capacitive sensor.

6. The patient support apparatus of claim 1, wherein the controller is configured to determine a control attribute associated with the user interface, the control attribute comprising one or more of force applied to the user interface, displacement of the user interface, velocity of the user interface, and acceleration of the user interface.

7. The patient support apparatus of claim 6, wherein the controller is configured to, based on the control attribute, control one or more of displacement of the patient support deck relative to the base, velocity in moving the patient support deck, and acceleration in moving the patient support deck.

8. The patient support apparatus of claim 1, wherein the user interface further comprises an indicator for indicating that the user interface is active to perform the function of the patient support apparatus, wherein the indicator comprises one or more of a visual indicator, a tactile indicator, and an audible indicator.

9. The patient support apparatus of claim 1, wherein the gesture sensing device comprises a camera for monitoring motion of the user relative to the user interface system.

10. A patient support apparatus comprising:
a support structure comprising:
a base, and
a patient support deck coupled to the base, the patient support deck comprising a patient support surface capable of articulating to adjust positioning of a patient supported thereon;
a lift system configured to adjust a height of the patient support deck relative to the base; and
a user interface system comprising an elongated member coupled to the support structure and a first user interface movably coupled to the elongated member and configured to be one or more of translated along the elongated member and rotated about the elongated member, the first user interface configured to receive inputs from a user and comprising a gesture sensing device for monitoring motion of the user, and including a controller to control operation of the lift system when a detected height of the patient support deck reaches a first threshold and to be inactive when the detected height of the patient support deck reaches a second threshold, and wherein the user interface system comprises a second user interface coupled to the support structure and configured to be active to generate an input signal upon receiving input to control operation of the lift system when the detected height of the patient support deck reaches the second threshold.

11. The patient support apparatus of claim 10, wherein the first user interface is disposed at a position that is higher relative to a position of the second user interface.

12. The patient support apparatus of claim 10, wherein the controller is configured to determine a control attribute associated with the first user interface, the control attribute comprising one or more of force applied to the first user interface, displacement of the first user interface, velocity of the first user interface, and acceleration of the first user interface.

13. The patient support apparatus of claim 12, wherein the controller is configured to, based on the control attribute, control one or more of displacement of the patient support deck relative to the base, velocity in moving the patient support deck, and acceleration in moving the patient support deck.

14. The patient support apparatus of claim 10, wherein the first user interface is configured to receive inputs to control operation of the lift system to adjust one or more of:
height of the patient support deck relative to the base; and
tilt of the patient support deck relative to the base.

15. The patient support apparatus of claim 10, wherein the first user interface is configured to receive inputs to control one or more of:
articulation of the patient support surface relative to the base;
movement of the patient support apparatus over a surface; and
activation of an alarm.

16. The patient support apparatus of claim 10, wherein the first user interface comprises a capacitive sensor interface.

17. The patient support apparatus of claim 10, wherein the user interface system further comprises an indicator for indicating that the first user interface is active to perform a function of the patient support apparatus, wherein the indicator comprises one or more of a visual indicator, a tactile indicator, and an audible indicator.

18. The patient support apparatus of claim 10, wherein the gesture sensing device comprises a camera for monitoring motion of the user relative to the user interface system.

* * * * *